United States Patent
Larsson et al.

(10) Patent No.: US 6,473,650 B1
(45) Date of Patent: Oct. 29, 2002

(54) EVOKED RESPONSE DETECTOR FOR A HEART STIMULATOR

(75) Inventors: Berit Larsson, Danderyd (SE); Asa Uhrenius, Stockholm (SE); Peter Andersson, Stockholm (SE); Göran Budgivars, Spanga (SE)

(73) Assignee: St. Jude Medical AB, Järfälla (SE)

( * ) Notice: Subject to any disclaimer, the term of this patent is extended or adjusted under 35 U.S.C. 154(b) by 0 days.

(21) Appl. No.: 09/719,738

(22) PCT Filed: Jun. 9, 1999

(86) PCT No.: PCT/SE99/01016
§ 371 (c)(1),
(2), (4) Date: Feb. 23, 2001

(87) PCT Pub. No.: WO99/65567
PCT Pub. Date: Dec. 23, 1999

(30) Foreign Application Priority Data

Jun. 16, 1998 (SE) .............................. 9802150

(51) Int. Cl.[7] .......................... A61N 1/37; A61N 1/365
(52) U.S. Cl. ....................................................... 607/28
(58) Field of Search ..................................... 607/27, 28

(56) References Cited

U.S. PATENT DOCUMENTS

| | | |
|---|---|---|
| 5,391,192 A | 2/1995 | Lu et al. |
| 5,417,718 A | 5/1995 | Kleks et al. |
| 5,431,693 A | 7/1995 | Schroeppel |
| 5,741,312 A | 4/1998 | Vonk et al. |
| 6,029,088 A * | 2/2000 | Budgifvars et al. ........... 607/27 |
| 6,052,622 A * | 4/2000 | Holmstrom ................... 607/28 |
| 6,144,881 A * | 11/2000 | Hemming et al. ............ 607/28 |
| 6,324,427 B1 * | 11/2001 | Florio ......................... 607/28 |

FOREIGN PATENT DOCUMENTS

EP    0 906 768    4/1999

OTHER PUBLICATIONS

"Comparison Of Unipolar And Bipolar Ventricular Paced Evoked Responses," Baig et al., Br. Heart J. vol. 68 (1992), pp. 398–402.

"Analysis of the Polarization and the Sensing Behaviour of Electrodes for Cardiac Pacemakers," Mund, Pacemaker Leads, Elsevier Science Publisher PV, 1991, pp. 503–509.

* cited by examiner

*Primary Examiner*—Joseph Pelham
(74) *Attorney, Agent, or Firm*—Schiff Hardin & Waite

(57) ABSTRACT

A heart stimulator has an evoked response detector for determining evoked response in the presence of polarization. The heart stimulator produces stimulation pulses of different amplitudes via a lead introduced to the heart of the patient. The evoked response detector measures an electrode signal picked up by the lead after each stimulation pulse. In order to set an evoked response threshold value, the pulse generator of the stimulator is controlled to deliver at least two stimulation pulses with different amplitudes, at least one of these stimulation pulses having a high amplitude that exceeds the stimulation threshold value. A measuring unit in the evoked response detector measures the picked up electrode signals, and a calculating unit in the evoked response detector calculates the polarization for the high stimulation amplitude and identifies a measured electrode signal for the lowest possible stimulation amplitude from the measured electrode signals. The evoked response detector also has an analyzing unit which sets a threshold value for the measured electrode signal from the calculated polarization and lowest possible stimulation amplitude.

4 Claims, 2 Drawing Sheets

EVOKED RESPONSE DETECTOR FOR A HEART STIMULATOR

BACKGROUND OF THE INVENTION

1. Field of the Invention

The present invention relates to an evoked response detector for a heart stimulator for determining evoked response in the presence of polarization, the heart stimulator having a pulse generator and control means for controlling the pulse generator to produce stimulation pulses of varying amplitudes, and a lead being intended to be introduced into the heart of a patient and connected to the pulse generator for delivering stimulation pulses to the heart, the evoked response detector includes measuring means for measuring the electrode signal picked up by the lead.

2. Description of the Prior Art

To reduce the energy consumption of heart stimulators an automatic threshold search function, a so called AUTOCAPTURE™ function, is used to maintain the energy of the stimulation pulses at a level just above that which is needed to effectuate capture, cf. e.g. U.S. Pat. No. 5,458,623. A reliable detection of the evoked response, which then is necessary, is, however, not a simple matter, especially when it is desired to sense the evoked response with the same electrode as the one delivering the stimulation pulses. This because of the fact that the evoked response potential is small in amplitude compared to the residual polarization charge. The residual charge decays exponentially but tends to dominate the evoked potential for several hundreds of milliseconds after the stimulation. If the polarization is too high, it could be wrongly interpreted by the evoked response detector as a capture, i.e. contraction of the heart. The AUTOCAPTURE™ algorithm could then by mistake adjust the output amplitude of the stimulation pulse to a value below the actual capture level, which will result in no capture. If the used pacing lead has significant polarization this could consequently disturb the autocapture function and result in loss of capture.

U.S. Pat. No. 5,417,718 discloses an autocapture system within an implantable pulse generator that automatically maintains the energy of a stimulation pulse at a level just above stimulation threshold level. The electrical post-stimulus signal of the heart following the delivery of a stimulation pulse is compared to a polarization template, determined during a capture verificastion test. A prescribed difference between a polarization template and the post-stimulus signal indcates capture.

A unipolar sensed evoked response signal differs from a bipolar sensed evoked response signal both in duration and amplitude, see M. W. Baig et al., "Comparison of Unipolar and Bipolar Ventricular Paced Evoked Responses", Br. Heart J. 1992, 68: 398–402. The duration of the evoked QRS complex is a measure of total ventricular polarization time in the area of the heart subtended by a sensing dipole, and it depends on the extension of the dipole. This means that the unipolar evoked response signal has a longer duration than the bipolar evoked response. Today's evoked response detectors are designed to detect the positive slope of the evoked response signal which occurs within a detection window, typically 15 to about 60 ms after the stimulation pulse, and is not suited for detection of the unipolar evoked response signal.

Thus there is mostly at least one significant slope in the bipolar measured IEGM signal, which makes it possible to discriminate the evoked response signal from slowly varying signals such as polarization signals. Thus in U.S. Pat. No. 5,431,693 a method of verifying capture of the heart by a cardiac pacemaker is described. Observing that the non-capture potential is exponential in form and the evoked capture potential, while generally exponential in form, has one or more small amplitude perturbations superimposed on the exponential wave form, these perturbations are enhanced for ease of detection by processing the wave form signal by differentiation to form the second derivative of the evoked response signal for analysis for the evoked response detection.

Unipolar detection of evoked response signal is, however, not possible by this technique. Abrupt slope changes or superimposed small-amplitude perturbations are levelled out if the measurements are made over the longer distance from AUTOCAPTURE™ function available today requires a bipolar ventricular lead for the evoked response detection, whereas stimulation can be accomplished also in unipolar mode.

It has become apparent that the true evoked response signal amplitude is fairly constant, independent of the stimulation pulse amplitude, i.e. the evoked response signal amplitude does not vary with the amplitude of the stimulation pulse (provided that the stimulation amplitude is above the stimulation threshold), whereas the electrode polarization is approximately linearly dependent on the stimulation pulse amplitude for a constant pulse duration, see European Application 0906768 and the description below in connection with FIG. 1. These circumstances make unipolar evoked response detection possible without measurement of the slope of any part of the signal picked up by the lead.

SUMMARY OF THE INVENTION

An object of the present invention is to provide a technique for setting the threshold value for evoked response detection for an evoked response detector, the function of which is based on the aforementioned principles.

This object is achieved in accordance with the principles of the present invention in a heart stimulator having a pulse generator and a control unit which controls the pulse generator to emit at least two stimulation pulses having different amplitudes, with one of these stimulation pulses having a high amplitude that exceeds the stimulation threshold value. The pulses are delivered to a heart via a lead connected to the pulse generator. An evoked response detector is also connected to the lead and includes a measuring unit which measures respective electrode signals picked up via the lead immediately following the aforementioned two stimulation pulses. In order to set an evoked response sensitivity, the evoked response detector includes a calculating unit which calculates the polarization $Pol_{high}$ for the high stimulation pulse and the measured electrode signal $U_{measlow}$ for the lowest possible stimulation amplitude. The evoked response detector also includes an analyzing unit which sets the threshold value $ER_{Limit}$ for the measured electrode signal for evoked response detection according to the equation $$ER_{Limit} = \frac{U_{measlow} - Pol_{high}}{n} + Pol_{high}$$

wherein n is a number greater than 1, preferably 1<n<10, provided that $U_{measlow} < Pol_{high}$ and $|U_{measlow} - Pol_{high}| > Y$, wherein Y is a predetermined value.

The detector according to the invention can be used also for unipolar detection of evoked response, which is an important advantage since unipolar leads are less complicated to manufacture and have longer working life than bipolar electrodes. Of course, the detector according to the invention can also be used for unipolar detection of evoked response by using bipolar electrodes in an unipolar mode of operation. The measurement could then be performed between the ring electrode and the casing of the heart stimulator, since severe difficulties in relation to the measurements are avoided if the tip electrode, which is used for stimulation, is not used for the subsequent measurements.

In an embodiment of the detector according to the invention the analyzing unit activates an automatic threshold search function of the control unit of the heart stimulator provided the conditions $U_{measlow} < POL_{high}$ and the $|U_{measlow} - POL_{high}| > Y$ are fulfilled. Thus in this way the use of heart stimulators, like pacemakers with AUTOCAPTURE™ function, can be extended also to patients with unipolar leads. For sensing evoked response in the unipolar configuration not only low polarization leads can consequently be used with AUTO CAPTURE™ pacemakers but also high polarization leads.

In another embodiment of the detector according to the invention the pulse generator is controlled to deliver a predetermined number of stimulation pulses of each amplitude $U_{1stim}$, $U_{2stim}$. The calculating unit calculates the mean or maximum amplitudes of the measured electrode signals $U_1$, $U_2$ picked by the lead after each pulse of the number of stimulation pulses, the mean or maximum amplitudes being used for setting the evoked response threshold value and for determining activation of said automatic threshold search function of the heart stimulator. In this way small variations in the picked up signals are suppressed.

DESCRIPTION OF PREFERRED EMBODIMENTS

The polarization of a pacemaker electrode can be described as $$Pol = \frac{U_{stim}}{\alpha} \times F(dur, RC_{output}) \quad (1)$$

where Pol denotes the polarization signal, $U_{stim}$ the pacemaker stimulation pulse amplitude, $\alpha$ is a constant, dur designates the duration of the stimulation pulse and $RC_{output}$ is a time constant of the pacemaker's output lead system, see Konrad Mund, "Analysis of the Polarization and the Sensing Behaviour of Electrodes for Cardiac Pacemakers", Pacemaker Leads, Elsevier Science Publishers BV, 991, pp. 503–509.

Thus, according to equation (1) above the polarization is a function of the duration dur of the stimulation pulse and the time constant $RC_{output}$. This means that if the duration dur of the stimulation pulse and the time constant $RC_{output}$ are constant for different stimulation pulse amplitudes the polarization Pol depends only on the stimulation pulse amplitude $U_{stim}$ and this dependency is linear.

Further, studies on animals show that the evoked response signal amplitude ER is roughly constant for different stimulation pulse amplitudes $U_{stim}$ and independent of the stimulation pulse duration dur, cf. the previously mentioned European Application No. 0906768.

Figure 1:
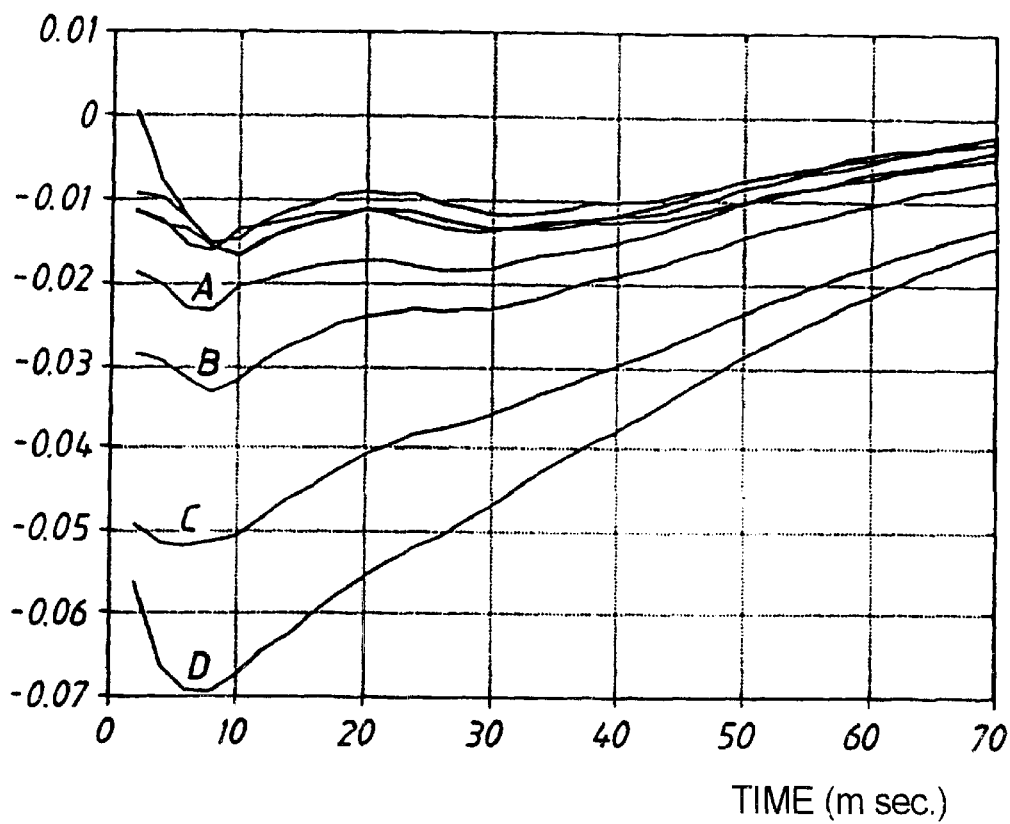
FIG. 1 shows measured electrode signals (IEGM) picked up for four different stimulation pulse amplitudes as a function of time, from immediately after the delivery of a stimulation pulse to 70 ms after the pulse, as well as the same signals with the polarization subtracted.

FIG. 1 shows the measured electrode signal (IEGM) or different stimulation amplitudes as a function of time. Thus the electrode signals are recorded from immediately after the delivery of a stimulation pulse, time 0, and until 70 msec after the stimulation. Curve A is obtained for a stimulation pulse amplitude of 0,6 V, curve B is obtained for a stimulation pulse amplitude of 1,5 V, curve C is obtained for a stimulation pulse amplitude of 3.0 V, and curve D for a stimulation pulse amplitude of 4.5 V.

Each curve A–D represents the sum of the evoked response signal and the polarization signal. As the evoked response signal is substantially constant it is apparent from FIG. 1 that the polarization signal varies significantly with the used stimulation pulse amplitude, the shown maximum variation amounting to approximately 50 mV.

The family of curves at the top of the figure represents the measured signals with subtracted polarization. As appears the curves are in fact concentrated in a narrow region, thus illustrating the above mentioned fact that the evoked response signal is substantially independent of the stimulation amplitude.

Figure 2:
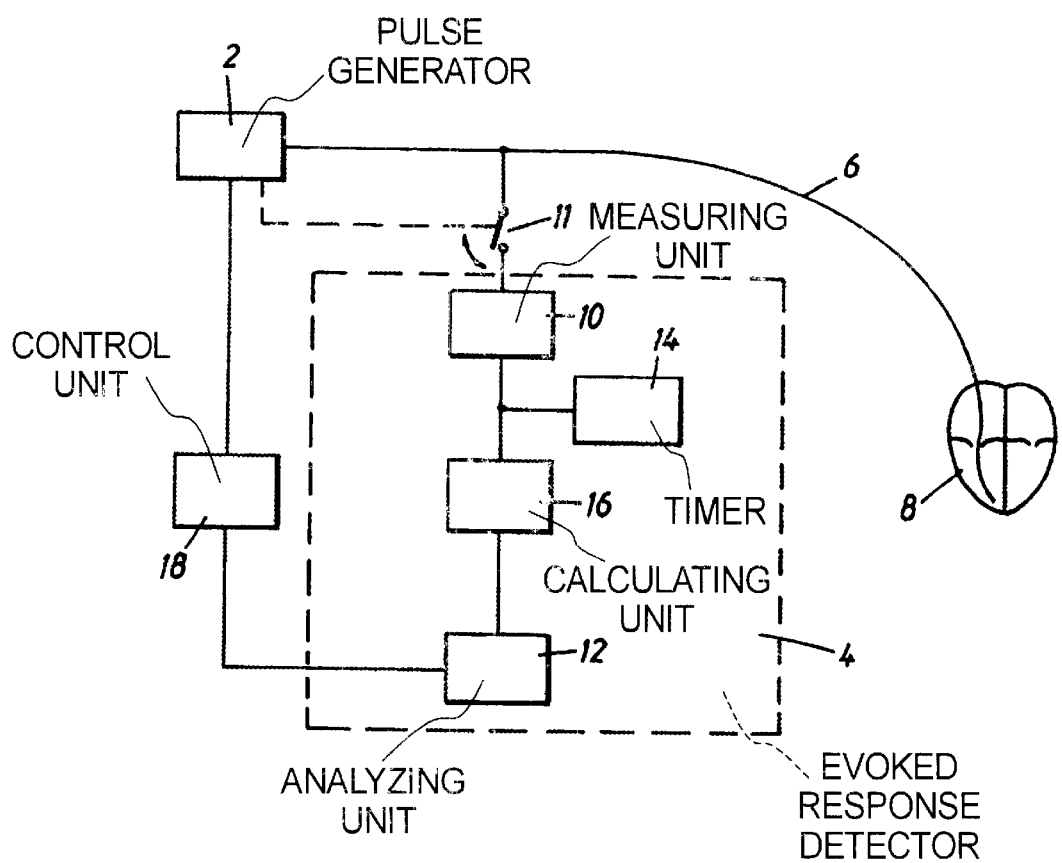
FIG. 2 is a block diagram of a heart stimulator constructed and operating in accordance with the principles of the present invention.

FIG. 2 shows a block diagram of the principal layout of a heart stimulator incorporating the detector according to the invention. The stimulator, includes a pulse generator 2 which, through a lead 6 is connected to the heart 8 of a patient. The pulse generator 2 is devised to produce stimulation pulses of varying amplitudes which through the lead 6 are transferred to the heart 8. The evoked response detector 4 includes an analog bandpass filter with a cut-off frequency of 1–130 Hz, and a measuring unit 10. The filtered measured signal is supplied to a calculating means 16 where the signal is sampled and digitized. Such a sampling and digitizing procedure is performed before the emission of each stimulation pulse and the mean value of these samples is calculated in the calculating unit 16 and represents the DC level. The stimulation pulse followed by the fast discharge pulse then occurs. A timer 14 are provided for blanking the evoked response detector to 15 msec of the stimulation pulse, whereupon the picked up IEGM signal is sampled and digitized. The sampling frequency can suitably be 512 Hz and the sampling occurs during an evoked response window of about 40 msec, determined by the timing means 14. This means that about 20 samples are collected for each stimulation. The DC level determined before the delivery of the stimulation pulse, is subtracted from each sample and the mean value of all 20 samples is calculated in the calculating unit 16. This mean amplitude of the picked up electrode signal is supplied to analyzing unit 12. A control unit 18 connected to the analyzing unit 12 and the pulse generator 2 for controlling the pulse generator 2 according to the signal received from the analyzing unit 12.

To determine the threshold value for evoked response detection $ER_{Limit}$ the following procedure is used.

It is assumed that the stimulation amplitude can be varied from 4.5 V to 0.3 V with an amplitude resolution of 0.3 V. Further information about the stimulation threshold value is supplied to the analyzing means 12 e.g. by way of a programmer.

Five stimulation pulses of 4.5 V are delivered and the picked up electrode signal after each stimulation pulse is sampled and digitized as described above. The less negative value or the mean value of these five electrode signals $U_{meas4.5}$ is stored.

If the stimulation threshold value is less than a predetermined value X, five stimulation pulses of an amplitude equal to the stimulation threshold value plus 0.3 V are delivered and the corresponding picked up electrode signals are treated as described above and the less negative value or the mean value of these five electrode signals are stored as $U_{measthresh+0.3}$.

The polarization for the stimulation amplitude $U_{stim}=4.5-(U_{stimthtresh+0.3})$ is given by the equation $$Pol_{4.5-(thresh+0.3)} = U_{meas4.5} - U_{measthresh+0.3} \quad (2)$$

The polarization for a stimulation amplitude of 0.3 V is given by the equation $$Pol_{0.3} = \frac{Pol_{4.5-(thresh+0.3)}}{K} \quad (3)$$

$$\text{where} \quad K = \frac{4.5 - (U_{stimthresh+0.3})}{0.3}$$

If the stimulation threshold value $U_{stimstresh}>X$ the procedure will be as follows.

Five stimulation pulses with an amplitude $U_{stimthtresh-0.3V}$ equal to the stimulation threshold value minus 0.3 V are delivered and the picked up electrode signal $U_{measthresh-0.3}$ is treated as described above and the mean value from the five stimulation pulses is stored as these stimulations will result in loss of capture the stored mean value will represent the polarization $Pol_{thresh-0.3}$.

The polarization for a stimulation pulse of 0.3 V can be calculated as $$Pol_{0.3} = \frac{Pol_{thresh-0.3}}{K}$$

$$\text{where} \quad K = \frac{U_{stimthresh-0.3}}{0.3}$$

The polarization for a stimulation pulse of 4.5 V can be calculated by multiplying $Pol_{0.3}$ by 15, that is $$Pol_{4.5} = 15 \times Pol_{0.3}.$$

The picked up electrode signal $U_{meas0.6}$ for a stimulation amplitude of 0.6 V can be calculated as follows.

$$U_{meas0.6} = U_{meas4.5} - 13 \times POL_{0.3}$$

This calculation is needed only if the stimulation threshold value is equal to or exceeds 0.6 V. If the stimulation threshold value equals 0.3 V $U_{meas0.6} = U_{measthres+0.3}$.

For setting the threshold value $ER_{Limit}$ for the measured electrode signal for evoked response detection the difference between $U_{meas0.6}$ and $Pol_{4.5}$ is studied. If $U_{meas0.6}<Pol_{4.5}$ and $|U_{meas0.6}-Pol_{4.5}|>Y$, where Y denotes a predetermined value, the threshold value is set as $$ER_{Limit} = \frac{U_{meas0.6} - Pol_{4.5}}{n} + Pol_{4.5}$$

where n denotes a figure>1, preferably 1<n <10.

Thus, if the measured electrode signal $U_{meas}<ER_{Limit}$ (the electrode signal is negative), capture is indicated and the AUTOCAPTURE™ function of the control means 18 is activated by the analyzing unit 12.

Figure 3:
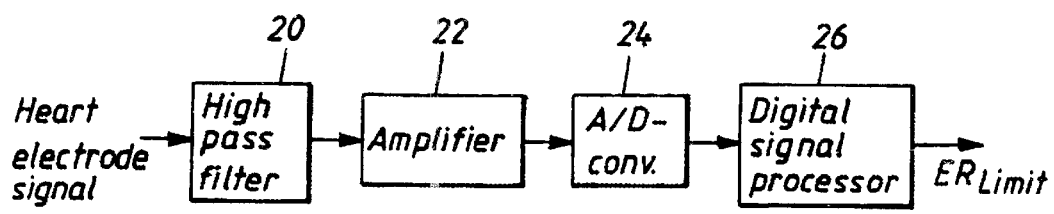
FIG. 3 is a block diagram of an embodiment of the evoked response detector constructed and operating in accordance with the principles of the present invention.

FIG. 3 shows in more detail an embodiment of the evoked response detector according to the invention. The heart electrode signal picked up by the lead 6 in FIG. 2 is then supplied to a highpass filter 20. An amplifier 22 and an AID-converter 24 are provided for amplifying and A/D-converting respectively the filtered signal. A digital signal processor 26 calculates the polarization $Pol_{high}$ for a high stimulation amplitude and the picked up electrode signal $U_{measlow}$ for the lowest stimulation amplitude and compares subsequently picked up electrode signals with a threshold value determined from the above mentioned quantities as described above to determine whether an evoked response is detected or not.

Thus in the embodiment shown in FIG. 3 the algorithm for determining the above mentioned threshold value is implemented in software by use of a microprocessor. Instead of a microprocessor this algorithm can also be implemented in random logic, which means realization by ordinary logic element, that is logic gates.

The detector according to the invention can also be implemented in the pacemaker electronics by use of switched capacitor (SC) technique where different capacitors serve as memory elements for storing the different electrode potentials and SC-adding, subtracting and multiplying circuits are used for performing the necessary calculations as explained above.

It is clear to those man skilled in the art that the embodiments described above with reference to FIGS. 2 and 3 should be considered merely as illustrating examples of the realization of the invention and that numerous modifications and variations are possible. Thus e.g. the figures given in the calculations described above are, of course, just examples. 4.5 V is an example of a high stimulation amplitude (preferably the highest available stimulation amplitude) and 0.6 V i s an example the pace lowest available stimulation amplitude. obviously these numeral values can be varied.

What is claimed is:

1. A heart stimulator comprising:

a pulse generator which emits stimulation pulses, each having an amplitude;

an electrode lead connected to said pulse generator and adapted for introduction int a patient to deliver said stimulation pulses to the patient's heart, and for picking up respective signals representing polarization of the heart immediately after each of said stimulation pulses;

a control unit connected to said pulse generator for controlling said pulse generator to emit at least two stimulation pulses having different amplitudes, at least one of said two stimulation pulses having a high amplitude which exceeds a stimulation threshold value for the heart;

an evoked response detector including a measuring unit connected to said electrode lead, a calculating unit connected to an output of said measuring unit, and an analyzing unit connected to an output of said calculating unit;

said measuring unit measuring respective signals picked up by said electrode lead immediately following said two stimulation pulses;

said calculating unit calculating a polarization $Pol_{high}$ for said stimulation pulse having a high amplitude and determining a measured signal $U_{measlow}$ from said electrode lead for a lowest possible stimulation amplitude; and said analyzing unit setting a threshold value $ER_{Limit}$ for a measured signal $U_{meas}$ for evoked response detection according to $$ER_{Limit} = \frac{U_{meslow} - Pol_{high}}{n} + Pol_{high}$$

wherein n is a number greater than 1 with $U_{measlow}$ being less than $Pol_{high}$, and with $|U_{measlow} - Pol_{high}| > Y$, wherein Y is a predetermined value.

2. A heart stimulator as claimed in claim 1 wherein said analyzing unit employs a value for n wherein $1 < n < 10$.

3. A heart stimulator as claimed in claim 1 wherein said control unit executes an automatic threshold search function activated by said analyzing unit when $U_{measlow}$ is less than $Pol_{high}$ and $|U_{measlow} - Pol_{high}|$ is greater than Y.

4. A heart stimulator as claimed in claim 1 wherein said control unit controls said pulse generator to emit said at least two stimulation pulses a predetermined number of times, and wherein said calculating unit calculates an average value for $Pol_{high}$ over said plurality of times and an average value for $U_{measlow}$ over said plurality of times, and wherein said analyzing unit uses the respective average values for $Pol_{high}$ and $U_{measlow}$ for determining $ER_{Limit}$.

* * * * *